US012593965B2

(12) United States Patent
Kuru et al.

(10) Patent No.: US 12,593,965 B2
(45) Date of Patent: Apr. 7, 2026

(54) ENDOSCOPE WITH A THREE-WIRE STEERING MECHANISM

(71) Applicant: AMBU A/S, Ballerup (DK)

(72) Inventors: Ismail Kuru, Munich (DE); Günter Wilhelm Schütz, Augsburg (DE)

(73) Assignee: AMBU A/S, Ballerup (DK)

( * ) Notice: Subject to any disclaimer, the term of this patent is extended or adjusted under 35 U.S.C. 154(b) by 218 days.

(21) Appl. No.: 18/571,395

(22) PCT Filed: Jun. 22, 2022

(86) PCT No.: PCT/EP2022/067040
§ 371 (c)(1),
(2) Date: Dec. 18, 2023

(87) PCT Pub. No.: WO2022/268891
PCT Pub. Date: Dec. 29, 2022

(65) Prior Publication Data
US 2024/0268641 A1 Aug. 15, 2024

(30) Foreign Application Priority Data
Jun. 22, 2021 (DE) ..................... 10 2021 116 162.2

(51) Int. Cl.
*A61B 1/00* (2006.01)
*A61B 1/005* (2006.01)
(52) U.S. Cl.
CPC .......... *A61B 1/0052* (2013.01); *A61B 1/0057* (2013.01)
(58) Field of Classification Search
CPC .. A61B 1/0052; A61B 1/0057; A61B 1/00042
See application file for complete search history.

(56) References Cited

U.S. PATENT DOCUMENTS

| | | | |
|---|---|---|---|
| 4,290,421 A | 9/1981 | Siegmund | |
| 4,947,827 A * | 8/1990 | Opie .................. | A61B 1/00073 600/149 |

(Continued)

FOREIGN PATENT DOCUMENTS

| | | |
|---|---|---|
| DE | 10222686 A1 | 11/2002 |
| DE | 19758596 B4 | 7/2005 |

(Continued)

OTHER PUBLICATIONS

German Search Report received for DE Application No. 10 2021 116 162.2, mailed on Feb. 23, 2022, 19 pages (10 pages of English Translation and 9 pages of Original Document).

(Continued)

*Primary Examiner* — Anh Tuan T Nguyen
*Assistant Examiner* — Rynae E Boler
(74) *Attorney, Agent, or Firm* — Faegre Drinker Biddle & Reath LLP

(57) ABSTRACT

An endoscope and a system including the endoscope and a monitor. The endoscope includes a handle; an insertion cord including an insertion tube, a bending section and a distal tip unit and defining an insertion cord axis; a steering mechanism configured to swivel the distal tip unit and including: a first input wheel and a second input wheel, both rotatably supported by the handle; and a first steering wire, a second steering wire and a third steering wire, all steering wires provided for controlling a bending movement of the bending section, connected to the first input wheel and/or the second input wheel, and extending through the insertion cord, and each steering wire radially spaced from the insertion cord axis and angularly spaced with respect to each other in the circumferential direction of the insertion cord.

18 Claims, 4 Drawing Sheets

(56)        References Cited

U.S. PATENT DOCUMENTS

| | | | |
|---|---|---|---|
| 9,820,634 B2 | 11/2017 | Simchony et al. | |
| 11,064,869 B2 | 7/2021 | Mcweeney et al. | |
| 2003/0023143 A1 | 1/2003 | Abe et al. | |
| 2006/0252993 A1 | 11/2006 | Freed et al. | |
| 2011/0295242 A1 | 12/2011 | Spivey et al. | |
| 2014/0046129 A1 | 2/2014 | Boutillette et al. | |
| 2014/0066706 A1 | 3/2014 | Mcweeney et al. | |
| 2015/0119801 A1 | 4/2015 | Grewe et al. | |
| 2015/0164305 A1* | 6/2015 | Kohno | A61B 1/00042 |
| | | | 600/149 |
| 2016/0316997 A1 | 11/2016 | Viebach et al. | |
| 2019/0239728 A1 | 8/2019 | Do et al. | |
| 2019/0374090 A1 | 12/2019 | Tanaka | |
| 2021/0251468 A1* | 8/2021 | Murata | A61B 1/0052 |
| 2021/0369082 A1 | 12/2021 | Durant et al. | |
| 2022/0079419 A1 | 3/2022 | Starkweather et al. | |
| 2022/0133130 A1 | 5/2022 | Bob | |
| 2023/0172440 A1* | 6/2023 | Schütz | A61B 1/00045 |
| | | | 600/109 |

FOREIGN PATENT DOCUMENTS

| | | | |
|---|---|---|---|
| DE | 102013226591 A1 | 6/2015 | |
| DE | 102016121056 A1 | 5/2018 | |
| DE | 102019102599 A1 | 8/2020 | |
| EP | 2508120 A1 | 10/2012 | |
| EP | 1737335 B1 | 5/2013 | |
| EP | 2417898 B1 | 12/2016 | |
| EP | 2883491 B1 | 4/2017 | |
| EP | 1956962 B1 | 9/2020 | |
| JP | 61-106125 A | 5/1986 | |
| JP | 2002-345742 A | 12/2002 | |
| WO | 2018/159555 A1 | 9/2018 | |
| WO | 2020/031293 A1 | 2/2020 | |
| WO | 2020/146812 A1 | 7/2020 | |

OTHER PUBLICATIONS

International Search Report and Written Opinion received for PCT Patent Application No. PCT/EP2022/067040, mailed on Oct. 4, 2022, 11 pages.

* cited by examiner

ENDOSCOPE WITH A THREE-WIRE STEERING MECHANISM

CROSS REFERENCE TO RELATED APPLICATIONS

This application is a National Phase entry under 35 U.S.C. § 371 of International Application No. PCT/EP2022/067040, filed Jun. 22, 2022, which claims the benefit of and priority from German Patent Application No. 10 2021 116 162.2, filed Jun. 22, 2021; the disclosures of said applications are incorporated by reference herein in their entirety.

TECHNICAL FIELD

The present disclosure relates to an endoscope comprising a proximal endoscope handle, an insertion cord extending from the endoscope handle and configured to be inserted into a patient's body cavity, the insertion cord comprising an insertion tube, a bending section and a distal tip unit and defining an insertion cord axis, and a steering mechanism configured to swivel/tilt the distal tip unit by bending the bending section, the steering mechanism comprising input wheels provided for receiving a rotational input by a user/an operator, and steering wires extending from the input wheels through the insertion cord.

RELATED ART

Steerable endoscopes often have a proximal endoscope handle with an operating wheel for operation by a user and a distal insertion cord including a bending section. The bending section can be bent or manipulated by pulling one or more pulling/steering wires, which extend into the insertion cord of the endoscope and which have distal portions attached to the bending section.

Typically, in an endoscope, which allows four-way-bending, four pulling wires may be provided, which are circumferentially offset with respect to each other by 90°, and pulling either one of the pulling wires/steering wires will result in a bending motion in a corresponding direction. Thus, two degrees of freedom (two bending planes) are provided with one degree of freedom comprising an up/down movement of the bending section effected by pulling one of two diametrically opposing pulling wires, and another degree of freedom comprising a left/right movement of the bending section effected by pulling one of two other diametrically opposing pulling wires. Since most endoscopes, which allow four-way-bending, are controlled via two degrees of freedom, most users are used to this kind of control.

Such endoscopes are generally provided with two steering wheels (manually operable wheels) at the endoscope handle, with one of the steering wheels being provided to control an up/down bending and the other one of the steering wheels being provided to control a left/right bending. Each steering wheel is connected to an input wheel, such as a sprocket or wire drum, which is connected to two of the steering wires, e.g. via a chain engaging the sprocket or by winding the wire around the drum. Thus, the steering wheel is rotated to rotate the input wheel, which results in a pulling of the one wire connected thereto and a loosening of the second wire connected thereto.

However, construction/assembly space in such endoscopes, particularly in the insertion cord, is very limited. Therefore, by providing four steering wires, the remaining space, which can be used for operational features such as a working channel and the like, is small.

An alternative solution for an endoscope, which allows four-way-bending, is known e.g. from U.S. Pat. No. 4,290, 421 A. Said endoscope has only three steering wires distributed evenly around a circumference of an insertion cord of the endoscope. All three wires are manipulated independently by lever operators or servomotors. Thus, a lot of construction/assembly space at the endoscope handle is required for accommodation of the lever operators or servomotors. As a result, the handle provides little space for additional operational features and/or has a heavier and bulkier design, making it difficult to handle for a user. Further, this solution is difficult to implement in an existing type of endoscope with two steering wheels at the handle or two other corresponding operating elements, such that the control of the four-way-bending has the same "feel" of control for a user as ordinary endoscopes with four steering wires. Moreover, this solution is associated with high costs and is thus in particular not suitable for single-use endoscopes.

BRIEF DESCRIPTION OF THE DISCLOSURE

In view of the above-described problems it is an object of the present disclosure to provide an endoscope which shall reduce or avoid the disadvantages of the prior art. In particular, it is an object of the disclosure to provide an endoscope with a steering mechanism, which provides two degrees of freedom and which provides more space for operational features.

This object is solved by an endoscope in accordance with claim 1 and by a system in accordance with claim 15. Advantageous aspects of the present disclosure are claimed in the dependent claims and/or are explained below.

In detail, the present disclosure relates to an endoscope comprising: a proximal endoscope handle; an insertion cord extending from the endoscope handle and configured to be inserted into a patient's body cavity, the insertion cord comprising an insertion tube, a bending section and a distal tip unit and defining an insertion cord axis; a steering mechanism configured to swivel the distal tip unit by bending the bending section; the steering mechanism comprising: a first input wheel and a second input wheel, the first input wheel and the second input wheel being rotatably supported and arranged within the endoscope handle and being provided for receiving a rotational input by a user; and exactly three steering wires, namely a first steering wire, a second steering wire and a third steering wire, wherein the first steering wire, the second steering wire and the third steering wire are provided for controlling a bending movement of the bending section, are connected to the first input wheel and/or the second input wheel, and extend through the insertion cord, and the first steering wire, the second steering wire and the third steering wire are each radially spaced from the insertion cord axis and are angularly spaced with respect to each other in the circumferential direction of the insertion cord.

Expressed in other words, an endoscope having an insertion cord/insertion shaft with a bending section is fitted with a steering mechanism for bending said bending section based on the principle of operatively connecting a first input wheel and a second input wheel (in short: input wheels) to the first steering wire, the second steering wire and (in particular via a connecting wire discussed in detail below) the third steering wire (in short: the steering wires), which are arranged at different angular positions with respect to the insertion cord axis, which extend through the insertion cord and which are connected to the bending section, in order to effect the bending of the bending section. That is, an operating force or torque for effecting said bending is applied to the input wheels and transmitted from the input wheels via at least one of the steering wires to the bending section. The number of steering wires being exactly three means that there are three steering wires and not one, two, four, five, six, etc. steering wires.

The steering wires have a spaced configuration. I.e. they are arranged at different positions along a circumference of the insertion cord, such that a bending of the bending section is achieved by pulling one or more of the steering wires. In particular, depending on which wires are operated, a bending of the bending section in at least two different bending planes (each defining two opposing bending directions), which intersect along the insertion cord axis and do not coincide/are non-parallel to each other, is achieved. Thus, the endoscope has a steering mechanism which provides two degrees of freedom.

Such a steering mechanism requires little construction/assembly space within the endoscope handle and/or within the insertion cord. Reducing the number of steering wires to three makes it possible to provide endoscopes having a reduced outer diameter, thereby allowing access to even smaller ducts of a body than in the related art. Alternatively, an enlarged inner diameter of the working channel may be achieved to provide access for larger tools. Additionally, the steering mechanism is assembled and manufactured in a simple and inexpensive manner. Alternatively or additionally the endoscope can have an advantageous ergonomic design, i.e. be less heavy and/or bulky (particularly the endoscope handle), for ease of handling. Further, operating a steering mechanism via two input wheels is a manner of operation, which is well-known to the user and a minimum amount of training is necessary. The function and "feel" of ordinary four-way steering control with two coaxial steering wheels at the handle can be maintained. Thus, user acceptance is expected to be high. Further, even if a wire is stuck, no full blockage of steering control occurs since the distal tip may still move diagonally.

The insertion cord axis is an axis, in particular a central axis, of the insertion cord extending in a proximal-distal-direction. Similarly, an axis of the first steering wire is an (central) axis of the first steering wire and/or an axis of the second steering wire is an (central) axis of the second steering wire and/or an axis of the third steering wire is an (central) axis of the third steering wire, respectively extending in a proximal-distal-direction.

Preferably, the first steering wire, the second steering wire and the third steering wire are each arranged at an equal distance (on the same circumference) from the insertion cord axis. The first input wheel and the second input wheel may be supported within a handle housing of the endoscope handle. The first input wheel may also be called a first control wheel. The second input wheel may also be called a second control wheel. The first input wheel and the second input wheel are rotatable and may have different shapes such as rectangular or polygonal block shapes. Preferably the input wheels have a rounded, further preferably circular, cross-sectional shape. The first input wheel and/or the second input wheel may comprise a drum. Alternatively or additionally, the first input wheel and/or the second input wheel may comprise a sprocket or a gear, engaging with a chain or the like attached to a proximal end of one of the steering wires. The steering wires may also be called control/pulling/angulation wires. The first input wheel and the second input wheel are preferably operable via separate operable elements, which can be operated individually and preferably independently from each other.

Preferably, the first input wheel is provided for receiving the rotational input by the user via a first manually operable element, e.g. a first handle wheel, connected to the first input wheel/control wheel via a first shaft (in a rotationally fixed manner). Further preferably, the second input wheel/control wheel is provided for receiving the rotational input by the user via a second manually operable element, e.g. a second handle wheel, connected to the second input wheel via a second shaft (in a rotationally fixed manner).

Advantageously, this makes it possible to control the bending of the bending section in an easily adjustable manner, which provides direct feedback to the user with regard to an actuating path and/or an actuating force/torque. Also, this manner of control is particularly well-known as a manner of operation of a steering mechanism. Thus, user acceptance of such a mechanism is high. The first handle wheel and the second handle wheel are preferably provided at an outside of the endoscope handle (the handle housing), such that they are easily accessible for the user. The first shaft and the second shaft extend preferably parallel to each other, further preferably coaxially to each other, i.e. one inside the other.

Preferably, the first input wheel and the second input wheel are translationally fixed with respect to the endoscope handle/the handle housing. That is, the first input wheel and the second input wheel may only rotate (not translate) with respect to the endoscope handle/the handle housing. In particular, the first shaft and the second shaft may be rotationally supported at fixed positions at the endoscope handle/the handle housing.

Preferably, the steering/control mechanism includes exactly two input wheels, namely the first input wheel and the second input wheel (i.e. not one, three, four, five, etc. input wheels), and thus preferably exactly two manually operable elements (i.e. not one, three, four, five, etc. operable elements).

Preferably, the first steering wire (a proximal end thereof) is connected to the first input wheel. In particular, a proximal end of the first steering wire is connected exclusively to the first input wheel (among the first input wheel and the second input wheel), i.e. not to the second input wheel. Further preferably, the second steering wire (a proximal end thereof) is connected to the second input wheel. In particular, a proximal end of the second steering wire is connected exclusively to the second input wheel (among the first input wheel and the second input wheel), i.e. not to the first input wheel. Further preferably, the third steering wire (via its proximal end) is connected to the first input wheel and to the second input wheel.

Expressed in other words, the first steering wire may be operable (in particular exclusively) via the first input wheel to bend the bending section in a first bending direction. The second steering wire may be operable (in particular exclusively) via the second input wheel to bend the bending section in a second bending direction. The third steering wire may be operable via the first input wheel to bend the bending section in a third bending direction opposite to the first bending direction. The third steering wire may be operated via the second input wheel to bend the bending section in a fourth bending direction opposite to the second bending direction.

Preferably, the steering mechanism further includes a connecting wire, which has a first end connected to the first input wheel and a second end connected to the second input wheel. Further preferably, the connecting wire is guided via a redirecting member connected to the third steering wire. Expressed in other words, the first input wheel and the second input wheel may be connected to each other via the connecting wire and may be connected to the third steering wire via the connecting wire and the redirecting member. Further, the connecting wire runs along/around/through the redirecting member, such that the redirecting member and the third steering wire connected thereto are movable/translatable/guided along (a central axis of) the connecting wire. A proximal end portion of the third steering wire may be connected to the redirecting member. I.e. the first input wheel, the second input wheel, the redirecting member, the connecting wire and the third steering wire may be connected to each other in a block-and-tackle-like manner.

The redirecting member may be configured to redirect the connecting wire. That is, an extending direction of the connecting wire may be changed at/by the redirecting member. The redirecting member may be located distally with respect to the first and second input wheels, such that the connecting wire extends from the first input wheel in a distal direction, is then guided around or through the redirecting member and then extends proximally to the second input wheel. The redirecting member may have a groove or a channel or a through hole for guiding the connecting wire. The redirecting member may be a passive drum, a sliding member or even a loop formed by a proximal end of the third steering wire.

Preferably, the redirecting member is accommodated in the endoscope handle so as to be translationally movable in an extending direction of the third steering wire. The endoscope handle (the handle housing) may comprise a guiding member such as a rail or groove for guiding the redirecting member, e.g. in a sledge-like manner. Alternatively, the redirecting member may be held at a distal position and/or may be pulled in a distal direction with respect to the first and second input wheels by the third steering wire. In this case, a position of the redirecting member may be determined by the connecting wire and the third steering wire, particularly without additional guidance in the extending direction of the third steering wire by the handle housing or the like.

Preferably, the first input wheel comprises a first wheel portion (also called a first drum) and a second wheel portion (also called a second drum), the first wheel portion having a first radius r1, the second wheel portion having a second radius r2, wherein the first radius r1 is different from, preferably smaller than, the second radius r2 and the first radius r1 and the second radius r2 are defined so as to have a specific first radius ratio r1/r2. Further preferably, the second input wheel comprises a third wheel portion (also called a third drum) and a fourth wheel portion (also called a fourth drum), the third wheel portion having a third radius r3 and the fourth wheel portion having a fourth radius r4, wherein the third radius r3 is different from, preferably smaller than, the fourth radius r4 and the third radius r3 and the fourth radius r4 are defined so as to have a specific second radius ratio r3/r4.

The first steering wire is preferably connected to the first wheel portion of the first input wheel and extends in a first circumferential direction/winding direction of the first input wheel. The second steering wire is preferably connected to the third wheel portion of the second input wheel and extends in a first circumferential direction/winding direction of the second input wheel. The connecting wire is preferably connected to the second wheel portion of the first input wheel and extends in a second circumferential direction/ winding direction (opposite to the first circumferential direction) of the first input wheel. Further, the connecting wire is preferably connected to the fourth wheel portion of the second input wheel and extends in a second circumferential direction/winding direction (opposite to the first circumferential direction) of the second input wheel.

The first wheel portion and the second wheel portion as well as the third wheel portion and the fourth wheel portion are preferably respectively connected to each other in a rotationally fixed manner and are preferably formed integrally.

During a rotation of the first input wheel, the first steering wire is moved in one direction among the distal and proximal directions (e.g. pulled in the proximal direction by being wound on the first wheel portion) by a first feeding distance/path length $\Delta a$ and the connecting wire is moved in the other direction among the distal and proximal directions (e.g. moved in the distal direction/loosened by being unwound from the second wheel portion) by a second feeding distance/path length $\Delta b'$1. Similarly, a length of movement of the second steering wire in the distal or proximal direction is a third feeding distance/path length $\Delta c$ and a length of movement of the connecting wire in the distal or proximal direction is a fourth feeding distance/path length $\Delta b'$2.

Preferably, a movement of the first, second and third steering wires and the connecting wire in a pulling direction/proximal direction is defined by positive feeding distances and a movement of the first, second and third steering wires and the connecting wire in a loosening direction/distal direction is defined by negative feeding distances. An overall feeding distance/path length $\Delta b'$ of the connecting wire may be defined by adding the second feeding distance $\Delta b'$1 and the fourth feeding distance $\Delta b'$2 ($\Delta b' = \Delta b'$1$+\Delta b'$2). Due to the redirection of the connecting wire by the redirecting member, a fifth feeding distance/path length of the third steering wire $\Delta b$, which is connected to the redirecting member, is half the overall feeding distance $\Delta b'$ of the connecting wire ($\Delta b = 0.5\ \Delta b'$).

Advantageously, this makes it possible to pull or loosen the first, second and third steering wires at different feeding distances. In this manner the first, third and fifth feeding distances $\Delta a$, $\Delta c$, $\Delta b$ respectively of the first, second and third steering wire can be adjusted with respect to their angular positions. Thereby, e.g. unnecessary slackening (i.e. (inappropriate/too much) loosening/movement in the distal direction) of the third steering wire when pulling the first steering wire by rotating the first input wheel can be avoided and, when a rotating direction of the first input wheel is inverted, high responsiveness of the bending control is ensured.

Preferably, (a central axis of) the second steering wire and (a central axis of) the insertion cord axis extend to define a first reference plane. The first specific radius ratio r1/r2 of the radius r1 of the first wheel portion with respect to the radius r2 of the second wheel portion of the first input wheel or drum may essentially equal half a ratio of a minimum (orthogonal) distance ra1 between the first steering wire and the first reference plane with respect to (divided by) a minimum distance rb1 between the third steering wire and the first reference plane $$\left( \frac{r1}{r2} = \frac{1}{2}\frac{ra1}{rb1} = -\frac{1}{2}\frac{\Delta a}{\Delta b}; \ \Delta c = 0 \right).$$

Further preferably, (a central axis of) the first steering wire and (a central axis of) the insertion cord axis extend to define a second reference plane. Further, the second specific radius ratio r3/r4 of the radius r3 of the third wheel portion with respect to the radius r4 of the fourth wheel portion of the second input wheel or drum may essentially equal half a ratio of a minimum (perpendicular/orthogonal) distance rc2 between the second steering wire and the second reference plane with respect to a minimum distance rb2 between the third steering wire and the second reference plane $$\left(\frac{r3}{r4} = \frac{1}{2}\frac{rc2}{rb2} = -\frac{1}{2}\frac{\Delta c}{\Delta b}; \Delta a = 0\right).$$

Expressed in other words, the minimum/perpendicular distance ra1 between the first steering wire and the first reference plane serves as a first lever for controlling the bending of the bending section in the first bending direction. Similarly, the minimum/perpendicular distance rc2 between the second steering wire and the second reference plane may serve as a second lever for controlling the bending of the bending section in the second bending direction. Similarly, the minimum/perpendicular distance rb1 between the third steering wire and the first reference plane may serve as a third lever for controlling the bending of the bending section in the third bending direction. Similarly, the minimum/perpendicular distance rb2 between the third steering wire and the second reference plane may serve as a fourth lever for controlling the bending of the bending section in the fourth bending direction. The first and the third bending directions may be defined by the first reference plane as being orthogonal thereto. Further, the second and the fourth bending directions may be defined by the second reference plane as being orthogonal thereto.

In summary, bending in a first bending direction perpendicular to a first reference plane, which includes a second steering wire, may be actuated by pulling a first steering wire via rotation of a first input wheel in a first rotating direction. Bending in a second bending direction perpendicular to a second reference plane, which includes the first steering wire, may be actuated by pulling the second steering wire via rotation of a second input wheel in a second rotating direction. Bending in a third bending direction opposite (and parallel) to the first bending direction and orthogonal to the first reference plane may be actuated by pulling a third steering wire via rotation of the first input wheel in a third rotating direction opposite to the first rotating direction. Bending in a fourth bending direction opposite (and parallel) to the second bending direction and perpendicular to the second reference plane may be actuated by pulling the third steering wire via rotation of the second input wheel in a fourth rotating direction opposite to the second rotating direction.

Due to this, adaption of the feeding distances of the steering wires to each other and to their respective angular positions is optimized. Advantageously, this results in further reduced/minimized slackening (i.e. (inappropriate/too much) loosening/movement in the distal direction) and, thus, better responsiveness of the bending control during a change of bending direction.

In case the first input wheel and the second input wheel are rotated simultaneously such that one of the second wheel portion and the fourth wheel portion unwinds the connecting wire whereas the other one of the second wheel portion and the fourth wheel portion winds up the connecting wire by the same feeding distances/wire lengths ($\Delta b'1=-\Delta b'2$), the third steering wire may be held static. Thus, a third reference plane may be provided, extending along the insertion cord axis and (an axis of) the third steering wire.

Preferably, the first end of the connecting wire is connected to a wheel portion having a larger radius among the first wheel portion and the second wheel portion, and the second end of the connecting wire is connected to a wheel portion having a larger radius among the third wheel portion and the fourth wheel portion. Thus, an overall feeding distance of the connecting wire during operation of the first input wheel and/or the second input wheel is relatively large, such that a required fifth feeding distance, which is large due to the block-and-tackle-like arrangement described above, may be achieved via a simple design.

Preferably, an angle (or angular offset in the circumferential direction) between two adjacent steering wires among the first steering wire, the second steering wire and the third steering wire with respect to the insertion cord axis is smaller than 180°, preferably between 20° and 160°, further preferably between 80° and 145°. In this manner, bending in each of the four bending directions (i.e. the first bending direction, the second bending direction, the third bending direction and the fourth bending direction) can be ensured.

Preferably, the insertion cord axis and one of the first steering wire, the second steering wire and the third steering wire (preferably the third steering wire) extend to define a symmetry plane, and the other ones of the first steering wire, the second steering wire and the third steering wire are arranged symmetrically with respect to the symmetry plane. In other words, one of the first, second and third steering wires (preferably the third) is arranged at the same angular distance with respect to the other two of the first, second and third steering wires. This allows a particularly simple mechanical design and intuitive handling, since an input required from the user (actuating path and/or actuating force required at the operable element) for controlling the bending section in the four bending directions is symmetric. In addition, assembly of the endoscope is simpler. In particular, if the angles between each pair of adjacent steering wires is essentially equal (i.e. 120°), assembly of the endoscope is particularly simple and cost-effective.

Preferably, an angle between the first steering wire and the second steering wire with respect to the insertion cord axis is between 85° and 95°, further preferably essentially 90°. That is, the first reference plane is orthogonal or nearly orthogonal (i.e. 90°+/−5°) to the second reference plane. Advantageously, this corresponds to bending directions typically achieved with a four-wire-steering mechanism. Thus, the steering mechanism according to the present disclosure can be handled similarly to the known four-wire-steering mechanism and user acceptance is high.

If the angle between the first steering wire and the second steering wire with respect to the insertion cord axis is 90° (+/−5°) as described above, the third steering wire is preferably arranged on the symmetry plane/at the same angular distance between the first and second steering wires. E.g. an angle between the first steering wire and the third steering wire and an angle between the second steering wire and the third steering wire with respect to the insertion cord axis are the same, particularly between 130° and 140°; further particularly 135°. In this manner, steering in any one of the bending directions requires similar amounts of actuating force/torque/path required as input from the user.

In other words, the first steering wire and the second steering wire are arranged at orthogonal positions in a cross-section of the bending section or the insertion cord, while the third steering wire is on a diagonal symmetry axis. Mathematical relations for the first degree of freedom in this case are $\Delta a=-\Delta b\sqrt{2}$, $\Delta c=0$, $r2=\sqrt{2}r1$, $\sqrt{2}\Delta a=-\Delta b'=-2\Delta b$. Also, mathematical relations for the second degree of freedom in this case are $\Delta c=-\Delta b\sqrt{2}$, $\Delta a=0$, $r4=\sqrt{2}r3$, $\sqrt{2}\Delta c=-\Delta b'=-2\Delta b$. If both the first input wheel and the second input wheel are operated, the fifth feeding distance of the third steering wire is calculated as $$\Delta b = -\frac{\Delta a + \Delta c}{\sqrt{2}}.$$

Optionally, an angle with respect to the insertion cord axis between one pair of adjacent steering wires among the first steering wire, the second steering wire and the third steering wire is between 190° and 140°, further preferably between 170° and 145°, further preferably between 160° and 150°. In other words, the levers (discussed in more detail below) for controlling the bending of the bending section in three of the four above defined bending directions are increased (maximized), whereas the lever for controlling the other one of the four bending directions is minimized. Due to this, it is possible to provide an endoscope, which is adapted to specific use cases by having up to three main/preferable bending directions, which are particularly easy to control.

Preferably, the first input wheel and/or the second input wheel is/are connected to, particularly equipped with, a braking or locking mechanism. During operation/actuation of one input wheel out of the first input wheel and the second input wheel, the braking or locking mechanism is configured to brake or lock a rotation of the other one of the first input wheel and the second input wheel transmitted via the connecting wire. Advantageously, providing such a braking or locking mechanism makes it possible to minimize or even to prevent a (unintentional) rotation of one of the first and second input wheels due to a torque or force transmitted thereto via the connecting wire, when the other one of the first and second input wheels is operated. I.e. unwanted interaction of control of the first and third bending directions with control of the second and fourth bending directions is minimized. Thus, a definite, accurate control of the steering mechanism is possible.

As a particularly simple and cost-efficient example, the braking or locking mechanism may comprise a friction increasing element provided between at least one rotating part of the steering mechanism and a rotationally fixed part of the endoscope handle. The friction increasing element may be mounted on the rotationally fixed part of the endoscope handle and/or at the at least one rotating part of the steering mechanism. For braking/locking a rotation of the first input wheel, the at least one rotating part of the steering mechanism may be the first shaft and/or the first operable element and/or the first input wheel. For braking/locking of a rotation of the second input wheel, the at least one rotating part of the steering mechanism may be the second shaft and/or the second operable element and/or the second input wheel. The rotationally fixed part of the endoscope handle is a part that does not rotate together with the at least one rotating part of the steering mechanism, e.g. a portion of the handle housing.

The braking or locking mechanism (torque brake) may be designed such that a static friction force between the at least one rotating part of the steering mechanism and the rotationally fixed part of the endoscope handle is at least as high as accumulated other forces transmitted to the static/not actively operated input wheel. Such forces are e.g. a torque or force transmitted via the connecting wire, resistance forces due to a friction between the steering wires and the insertion cord, particularly wire sheaths accommodating the steering wires, and reactive forces transmitted during bending, since the steering wires are connected to each other via their connection to the bending section.

Preferably, the endoscope is a single-use endoscope. I.e. the endoscope is structured and assembled in a simple, cost-efficient manner and/or dimensioned with regard to the strain of a single use. Thus, the endoscope can be provided in a safely sterile packaging. Further, costs for sterilisation and/or disinfection may be saved and dangers of incomplete sterilisation and/or disinfection may be avoided.

Further, the object is achieved by a system comprising an endoscope as described above and a monitor connectable to the endoscope.

BRIEF DESCRIPTION OF FIGURES

The following figures illustrate exemplary embodiments of the disclosure. The disclosure is not limited to the embodiments described below. Other embodiments, combinations of embodiments and modifications may be provided within the scope of protection defined by the claims.

DETAILED DESCRIPTION OF PREFERRED EMBODIMENTS

Figure 1:
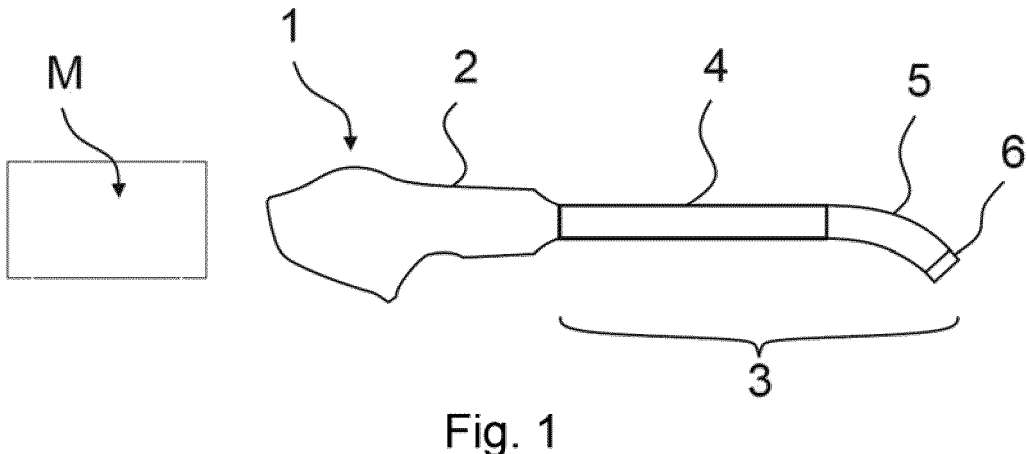
FIG. 1 shows a schematic view of a system comprising an endoscope and a monitor according to the present disclosure.

FIG. 1 shows a schematic view of an endoscope 1, which is preferably a single-use endoscope. The endoscope 1 has a proximal endoscope handle 2 and an insertion cord 3 extending distally from the endoscope handle 2. The insertion cord 3 has an insertion tube 4 connected to the endoscope handle 2. The insertion cord 3 further includes a bending section 5 connected to a distal end of the insertion tube 4 and a distal tip unit 6 connected to a distal end of the bending section 5. The insertion cord 3 has a central axis/insertion cord axis 7. The bending section 5 is configured to perform a bending/pivoting/swivelling movement in four different, preferably orthogonal, directions. This enables a steering of the endoscope 1. The bending/pivoting/swivelling movement is controlled by a steering mechanism according to any one of the embodiments described in detail below, including a first steering wire 8a, a second steering wire 8c and a third steering wire 8b (in short: the steering wires 8a, 8c, 8b), which extend through the insertion cord 3. In a neutral position, the bending section 5 is unbent by the steering mechanism, preferably straight/in alignment with the insertion tube 4.

At the distal tip unit 6, image capturing means such as a miniature video camera and illuminating means such as light-emitting diodes or optical fibers connected to a proximal source of light are arranged/installed, such that the patient's body cavity can be illuminated and inspected. An image captured by the image capturing means can be shown on a monitor M. The monitor M is provided separately from and connectable with the endoscope 1.

Figure 2:
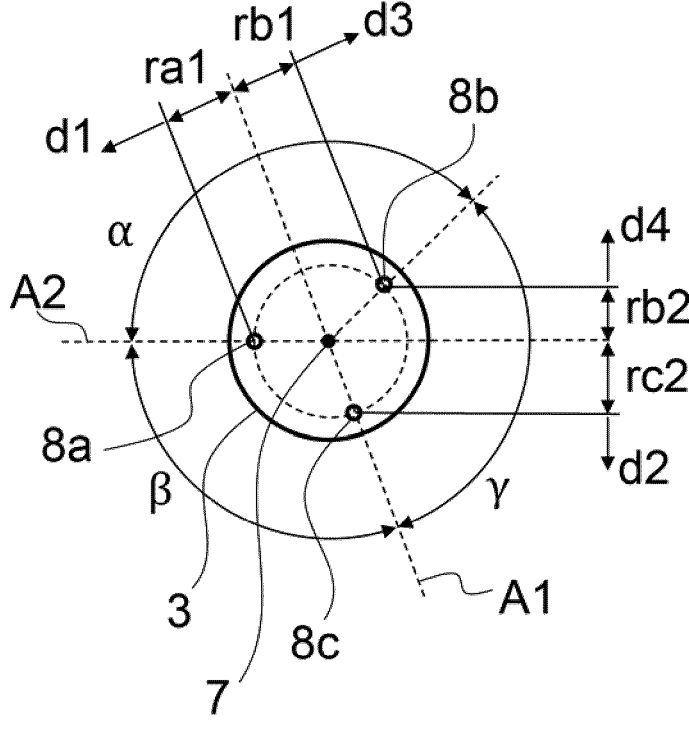
FIG. 2 schematically illustrates a cross-sectional view of an insertion cord of an endoscope according to a first embodiment of the present disclosure.

FIG. 2 schematically shows a cross-sectional view of an insertion cord 3 (e.g. a bending section 5) according to a first embodiment of the present disclosure. This view illustrates geometric parameters, which are relevant to the calculation of the steering mechanism.

In FIG. 2, first, second and third steering wires 8$a$, 8$c$, 8$b$ are arranged at an equal distance from the insertion cord axis 7. Further, the first, second and third steering wires 8$a$, 8$c$, 8$b$ are distributed in a circumferential direction of the insertion cord 3 and have different angular positions. With respect to the insertion cord axis 3, a first angle $\alpha$ is formed between the first steering wire 8$a$ and the third steering wire 8$b$, a second angle $\beta$ is formed between the first steering wire 8$a$ and the second steering wire 8$c$ and a third angle $\gamma$ is formed between the second steering wire 8$c$ and the third steering wire 8$b$. The first, second and third angles $\alpha$, $\beta$, $\gamma$ may e.g. be equal (120°).

The insertion cord axis 7 and a central axis of the second steering wire 8$c$ extend to define a first reference plane A1. Further, the insertion cord axis 7 and a central axis of the first steering wire 8$a$ extend to define a second reference plane A2. The first steering wire 8$a$ extends parallel to the first reference plane A1 at a first distance ra1, which defines a first lever for bending the bending section in a first bending direction d1 by pulling the first steering wire 8$a$. The second steering wire 8$c$ extends parallel to the second reference plane A2 at a second distance rc2, which defines a second lever for bending the bending section in a second bending direction d2 by pulling the second steering wire 8$c$. The third steering wire 8$b$ extends parallel to the first reference plane A1 at a third distance rb1, which defines a third lever for bending the bending section in a third bending direction d3 by pulling the third steering wire 8$b$. The third steering wire 8$b$ further extends parallel to the second reference plane A2 at a fourth distance rb2, which defines a fourth lever for bending the bending section in a fourth bending direction d4 by pulling the third steering wire 8$b$. The first to fourth distances ra1, rc2, rb1, rb2 are measured orthogonally with respect to the corresponding one of the reference planes.

Figure 3:
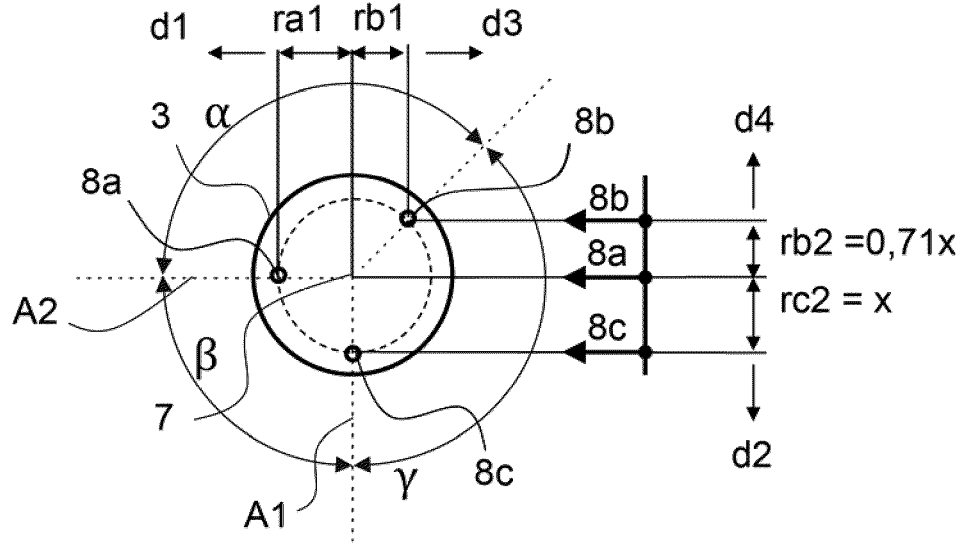
FIG. 3 schematically illustrates a cross-sectional view of an insertion cord of an endoscope according to a second embodiment of the present disclosure.

FIG. 3 schematically shows a cross-sectional view of an insertion cord 3 (e.g. bending section 5) according to a second embodiment of the present disclosure. The second embodiment corresponds to the first embodiment except for the angular positions of the steering wires 8$a$, 8$c$, 8$b$. In detail, the second angle $\beta$ defined by the first and second steering wires 8$a$, 8$c$ with respect to the insertion cord axis 7 is 90°. The first angle $\alpha$ defined by the third steering wire 8$b$ and the first steering wire 8$a$ and the third angle $\gamma$ defined by the third steering wire 8$b$ and the second steering wire 8$c$ are each 135°. Thus, the first and second references planes A1 and A2 are orthogonal to each other and the first and third bending directions d1, d3 are orthogonal to the second and fourth bending directions d2, d4. The first distance ra1 and the second distance rc2 are equal to each other, corresponding to a radial distance "x" of the first and second steering wires 8$a$, 8$c$ from the insertion cord axis 7. The third distance rb1 and the fourth distance rb2 are equal to each other, in this embodiment calculated as $x/\sqrt{2}\approx0.71x$. In FIG. 3, on the right hand side, a side view of the cross-section is shown, illustrating a position of the steering wires 8$a$, 8$c$, 8$b$ in accordance with said side view.

Figure 4:
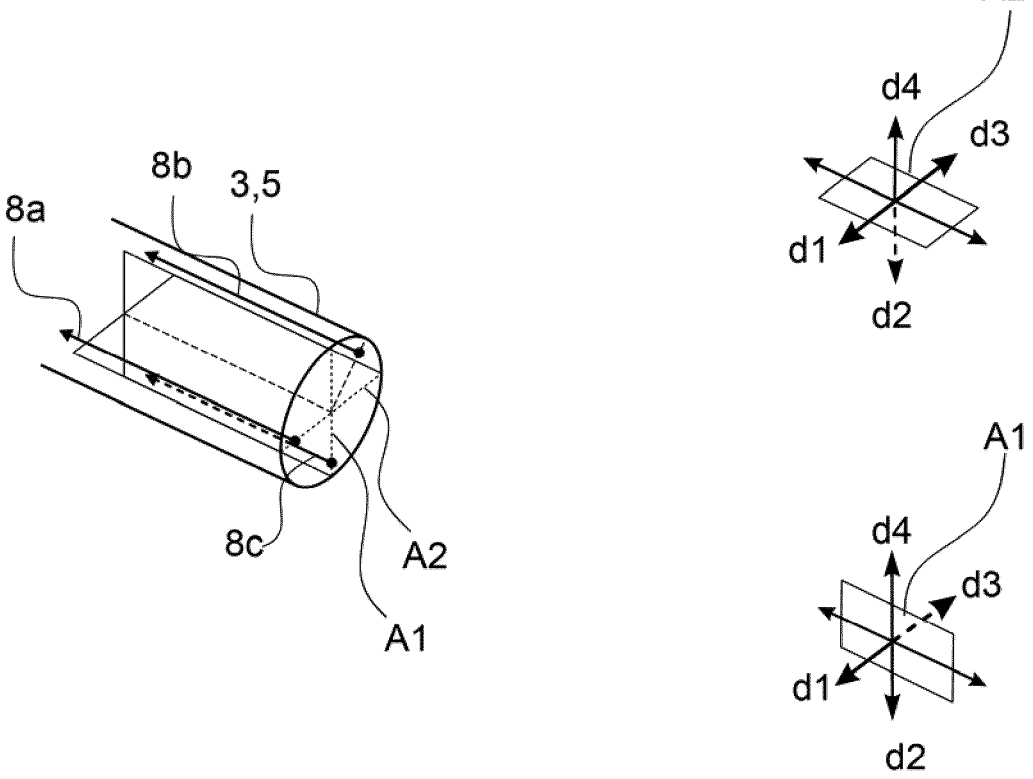
FIG. 4 schematically shows a perspective view of a portion of an insertion cord according to the second embodiment.

In FIG. 4, a portion of the insertion section 3 or bending section 5 of FIG. 3 is shown in a perspective view from a distal direction. As an example, the first reference plane A1 may be called a vertical plane, with the second bending direction d2 being a direction down and the fourth bending direction d4 being a direction up. Accordingly, the second reference plane A2 may be called a horizontal plane, with the first bending direction d1 being a direction to the right and the third bending direction d3 being a direction to the left.

Figure 5:
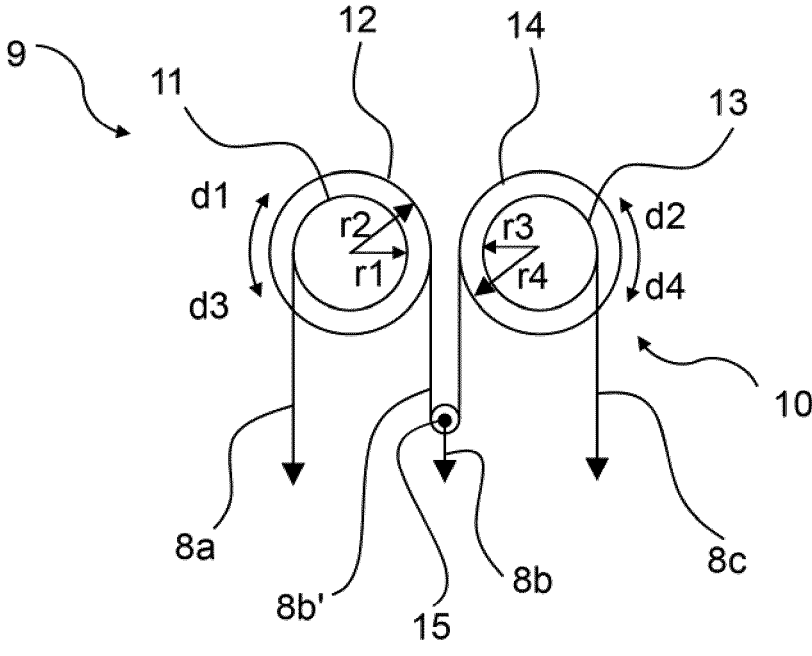
FIG. 5 schematically shows a proximal part of the steering mechanism according to the first or second embodiment.

FIG. 5 schematically shows a proximal part of the steering mechanism according to the first or second embodiment. The steering mechanism has a first control wheel/input wheel 9 for controlling the bending in the first and third bending directions d1, d3 and a second control wheel/input wheel 10 for controlling the bending in the second and fourth bending directions d2, d4. Rotating directions which correspond to the four bending directions d1, d2, d3 and d4 are indicated by arrows in FIG. 5. The first and second input wheels 9, 10 are rotatable with respect to each other and are individually controllable by a user. The first input wheel 9 has a first wheel portion 11 or a first drum and a second wheel portion 12 or a second drum, which are connected to each other in a rotationally fixed manner, preferably integrally. The second input wheel 10 has a third wheel portion 13 or a third drum and a fourth wheel portion 14 or fourth drum, which are connected to each other in a rotationally fixed manner, preferably integrally.

The first wheel portion 11 is connected to the first steering wire 8$a$ in such a manner, that the first steering wire 8$a$ is/can be wound around the first wheel portion 11 in a first circumferential direction thereof. The first steering wire 8$a$ extends distally from the first wheel portion 11. The second wheel portion 12 is connected to a connecting wire 8$b'$ in such a manner, that the connecting wire 8$b'$ is/can be wound around the second wheel portion 12 in a second (opposite to the first) circumferential direction thereof. The connecting wire 8$b'$ extends distally from the second wheel portion 12, is guided around a passive wheel or drum serving as a redirecting member 15 and then extends proximally to the second input wheel 10. There, the connecting wire 8$b'$ is connected to the fourth wheel portion 14 in such a manner, that the connecting wire 8$b'$ is/can be wound around the fourth wheel portion 14 in a first circumferential direction thereof. The second steering wire 8$c$ is connected to the third wheel portion 13 in such a manner, that the second steering wire 8$c$ is/can be wound around the third wheel portion 13 in a second (opposite to the first) circumferential direction thereof. The second steering wire 8$c$ extends distally from the third wheel portion 13.

The redirecting member 15 has a fifth wheel portion for guiding the connecting wire 8$b'$ in a translational manner. The fifth wheel portion can be freely designed and does not relate to the radii of the first, second, third and fourth wheel portions. The redirecting member 15 is connected to a proximal end portion of the third steering wire 8$b$. The third steering wire 8$b$ extends distally from the redirecting member 15. Thus, the first and second input wheels 9, 10, the redirecting member 15, the connecting wire 8$b'$ and the third steering wire 8$b$ are arranged in a block-and-tackle-like manner. A feeding distance/path length/moving distance of the third steering wire 8$b$ due to a rotation of the first and/or second input wheels 9, 10 is half of the feeding distance/path length/moving distance of the connecting wire 8*b'*.

The first input wheel portion 11 has a first radius r1. The second wheel portion 12 has a second radius r2, which is larger than the first radius r1. The first radius r1 divided by the second radius r2 defines a first radius ratio r1/r2. The first radius ratio r1/r2 depends on the angular position of the steering wires 8*a*, 8*c*, 8*b* and corresponds to half a ratio of the first distance ra1 divided by the third distance rb1

$$\left(\frac{r1}{r2} = \frac{1}{2}\frac{ra1}{rb2}\right).$$

The third input wheel portion 13 has a third radius r3. The fourth wheel portion 14 has a fourth radius r4, which is larger than the third radius r3. The third radius r3 divided by the fourth radius r4 defines a second radius ratio r3/r4. The second radius ratio r3/r4 depends on the angular position of the steering wires 8*a*, 8*c*, 8*b* and corresponds to half a ratio of the second distance rc2 divided by the fourth distance rb2

$$\left(\frac{r3}{r4} = \frac{1}{2}\frac{rc2}{rb2}\right).$$

According to the second embodiment, the first radius ratio and the third radius ratio are equal, in particular $1/\sqrt{2}$. Preferably, the first radius r1 is equal to the third radius r3 and the second radius r2 is equal to the fourth radius r4.

Figure 6:
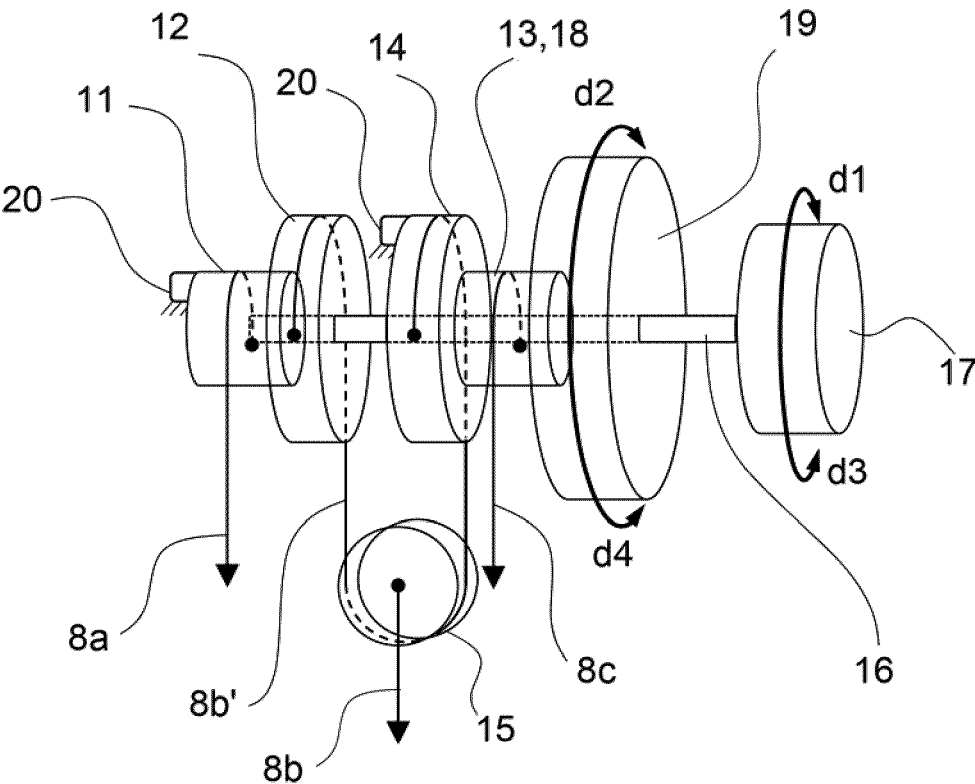
FIG. 6 illustrates an assembled arrangement of the proximal part of the steering mechanism according to the first or second embodiment.

FIG. 6 illustrates an assembled arrangement of the proximal part of the steering mechanism according to the first or second embodiment. The first input wheel 9 is rotationally fixed to an inner end portion of a first shaft 16 arranged inside the endoscope handle 2. The other end portion of the first shaft 16 is rotationally fixed to a first handle wheel 17 as a first manually operable element outside of a housing of the endoscope handle 2. The second input wheel 10 is rotationally fixed to an inner end portion of a second shaft 18 (in this example, the third wheel portion 13 double-functions as the second shaft 18) and is arranged inside the endoscope handle 2. The other end portion of the second shaft 18 is rotationally fixed to a second handle wheel 19 as a second manually operable element outside of a housing of the endoscope handle 2. The first shaft 16 extends coaxially to and through the second shaft 18. In this case, the redirecting member 15 is arranged in a side view, in particular with its axis being inclined/skewed or perpendicular with respect to the first and second shafts. Further, friction increasing elements 20, which contact both a static part of the endoscope housing 2 and at least one rotating part of the steering mechanism (in this case, the first input wheel 9 and the second input wheel 10), are provided as a braking or locking mechanism. Thus, when e.g. the first input wheel 9 is operated, the friction increasing element 20 which contacts the second input wheel 10 will prevent or brake a rotation of the second input wheel 10, which may occur due to a transmission of force or torque via the connecting wire 8*b'* from the first input wheel 9 to the second input wheel 10.

Figure 7:
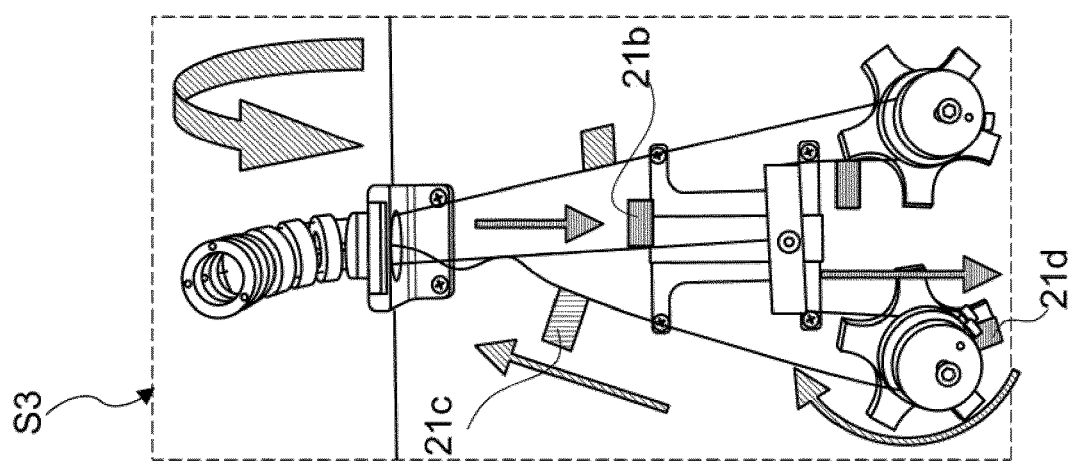
FIG. 7 illustrates an operation of the steering mechanism according to the second embodiment.

FIG. 7 illustrates three views of different states S1, S2, S3 of the steering mechanism according to the second embodiment during an operation in the manner of a test set-up. The steering mechanism shown in FIG. 7 basically corresponds to the steering mechanism shown in FIGS. 3 to 6. The bending section 5 includes a plurality of segments, which are connected to each other in a chain-like arrangement via joints/hinges in a known manner, such that bending of the bending section 5 in four bending directions can be achieved. In this example, a sledge or sliding member is provided as the redirecting member 15, which is guided along a guiding rail 22 to move in the extending direction of the third steering wire 8*b*.

In the first operating state S1 according to the left-hand view, the steering mechanism is shown in a neutral (i.e. unbent) position. For better visibility, complete reference signs are only shown in this illustration of the neutral position. Marker flags 21*a*, 21*b*, 21*c* are respectively fixed to the first, second and third steering wires 8*a*, 8*c*, 8*b* and two additional marker flags 21*d* are fixed to the connecting wire 8*b'* on either side of the redirecting member 15 in order to illustrate their movement/feeding distances.

In the second operating state S2 according to the middle view, a bending of the bending section 5 in the first bending direction d1 (e.g. to the right with reference to FIG. 4) is shown. In this case, the second input wheel 10 is static. The first input wheel 9 is rotated to pull the first steering wire 8*a* by a positive feeding distance indicated by the corresponding marker flag 21*a* and arrow. Simultaneously, the connecting wire 8*b'* is loosened (i.e. unwound) by a negative feeding distance as indicated by the corresponding marker flag 21*d* and arrow. That is, a free (unwound) length of the connecting wire 8*b'* between the first and second input wheels 9, 10 is increased. Due to the bending movement of the bending section, the third steering wire 8*b* is pulled in the distal direction as indicated by the corresponding marker flag 21*b* and arrow. Since the connecting wire 8*b'* is loosened, the third steering wire 8*b* pulls the redirecting member 15 in the distal direction. In consequence, the redirecting member pulls the connecting wire 8*b'*, translating relative thereto.

In the third operating state S3 according to the right-hand view, a bending of the bending section 5 in the fourth bending direction d4 (e.g. upwards with reference to FIG. 4) is shown. In this case, the first input wheel 9 is held static. The second input wheel 10 is rotated to pull the connecting wire 8*b'* by another positive feeding distance indicated by the corresponding marker flag 21*d* and arrow. Due to this, the free length of the connecting wire 8*b'* between the first and second input wheels 9, 10 is shortened. The connecting wire 8*b'* translates relative to the redirecting member 15, pulling the redirecting member 15 and the third steering wire 8*b* connected thereto in the proximal direction as indicated by marker flag 21*b* and arrow. Simultaneously, the second steering wire 8*c* is loosened (i.e. unwound) by another negative second feeding distance as indicated by the corresponding marker flag 21*c* and arrow. Due to the bending movement of the bending section, the second steering wire 8*c* is pulled in the distal direction.

LIST OF REFERENCE NUMBERS

1 Endoscope
2 Endoscope handle
3 Insertion cord
4 Insertion tube
5 Bending section
6 Distal tip unit
7 Insertion cord axis
8*a* First steering wire
8*b* Third steering wire
8*c* Second steering wire
8*b* Connecting wire
9 First input wheel/first control wheel
10 Second input wheel/second control wheel

11 First wheel portion/first drum
12 Second wheel portion/second drum
13 Third wheel portion/third drum
14 Fourth wheel portion/fourth drum
15 Redirecting member/passive wheel or drum/fifth wheel portion/fifth drum
16 First shaft
17 First manually operable element/first handle wheel
18 Second shaft
19 Second manually operable element/second handle wheel
20 Braking or locking mechanism/friction increasing element.
21*a*-21*d* Marker flags for first, second and third steering wires and connecting wire
22 Guiding rail/guiding
α, β, γ First angle, second angle and third angle
M Monitor
A1, A2 First and second reference planes
ra1 First distance
rc2 Second distance
rb1 Third distance
rb2 Fourth distance
d1-d4 First to fourth bending directions
r1-r4 First to fourth radiuses
S1, S2, S3 First, second and third operating states

The invention claimed is:

1. An endoscope comprising:
a handle;
an insertion cord extending from the handle and configured to be inserted into a patient's body cavity, the insertion cord comprising an insertion tube, a bending section and a distal tip unit and having an insertion cord axis;
a steering mechanism configured to swivel the distal tip unit by bending the bending section, the steering mechanism comprising:
a first input wheel comprising a first wheel portion having a first radius and a second wheel portion having a second radius different than the first radius, the first wheel portion being connected to the second wheel portion in a rotationally fixed manner;
a second input wheel comprising a third wheel portion having a third radius and a fourth wheel portion having a fourth radius different from the third radius, the third wheel portion being connected to the fourth wheel portion in a rotationally fixed manner, the first input wheel and the second input wheel being rotatably supported by the handle and being provided for receiving a rotational input by a user;
a connecting wire; and
exactly three steering wires, including a first steering wire, a second steering wire and a third steering wire, the three steering wires extending through the insertion cord to control a bending movement of the bending section,
wherein the first steering wire is connected to the first wheel portion,
wherein the second steering wire is connected to the third wheel portion,
wherein the connecting wire is connected to the second wheel portion and to the fourth wheel portion, and
wherein the first steering wire, the second steering wire and the third steering wire are each radially spaced from the insertion cord axis and are angularly spaced with respect to each other in a circumferential direction of the insertion cord.

2. The endoscope of claim 1, wherein the steering mechanism includes exactly two input wheels comprising the first input wheel and the second input wheel.

3. The endoscope of claim 1, wherein the steering mechanism further includes a redirecting member connected to the third steering wire, the connecting wire being guided via the redirecting member.

4. The endoscope of claim 3, wherein the redirecting member is positioned in the handle so as to be translationally movable in an extending direction of the third steering wire.

5. The endoscope of claim 1, wherein:
the first steering wire extends in a first circumferential direction of the first input wheel, the second steering wire extends in a first circumferential direction of the second input wheel, the connecting wire extends in a second circumferential direction of the first input wheel, and the connecting wire extends in a second circumferential direction of the second input wheel.

6. The endoscope of claim 5, wherein:
the second steering wire and the insertion cord axis extend to define a first reference plane,
a ratio of the first radius to the second radius defines a first radius ratio,
the first radius ratio essentially equals half a ratio of a minimum distance between the first steering wire and the first reference plane with respect to a minimum distance between the third steering wire and the first reference plane,
the first steering wire and the insertion cord axis extend to define a second reference plane,
a ratio of the third radius to the fourth radius defines a second radius ratio, and
the second radius ratio essentially equals half a ratio of a minimum distance between the second steering wire and the second reference plane with respect to a minimum distance between the third steering wire and the second reference plane.

7. The endoscope of claim 1, wherein:
the second radius is larger than the first radius, and
the fourth radius is larger than the third radius.

8. The endoscope of claim 7, wherein the first input wheel and/or the second input wheel is/are connected to a braking or locking mechanism which, during operation of one input wheel out of the first input wheel and the second input wheel is configured to brake or lock a rotation of the other one of the first input wheel and the second input wheel transmitted via the connecting wire.

9. The endoscope of claim 8, wherein the insertion cord axis and one of the first steering wire, the second steering wire and the third steering wire extend to define a symmetry plane and the other ones of the first steering wire, the second steering wire and the third steering wire are arranged symmetrically with respect to the symmetry plane.

10. The endoscope of claim 9, wherein an angle between two adjacent steering wires among the first steering wire, the second steering wire and the third steering wire with respect to the insertion cord axis is smaller than 180°.

11. The endoscope of claim 10, wherein an angle between the first steering wire and the second steering wire with respect to the insertion cord axis is between 85° and 95°.

12. The endoscope of claim 1, wherein the first input wheel and the second input wheel are translationally fixed with respect to the handle.

13. The endoscope of claim 12, wherein:
the first input wheel is configured to receive the rotational input by the user via a first manually operable element connected to the first input wheel via a first shaft, and the second input wheel is configured to receive the rotational input by the user via a second manually operable element connected to the second input wheel via a second shaft.

14. An endoscope comprising:

a handle;

an insertion cord extending from the handle and configured to be inserted into a patient's body cavity, the insertion cord comprising an insertion tube, a bending section and a distal tip unit and having an insertion cord axis;

a steering mechanism configured to swivel the distal tip unit by bending the bending section, the steering mechanism comprising:

a first input wheel and a second input wheel, the first input wheel and the second input wheel being rotatably supported by the handle and being provided for receiving a rotational input by a user; and exactly three steering wires, including a first steering wire, a second steering wire and a third steering wire, the three steering wires extending through the insertion cord and being connected to the first input wheel and/or the second input wheel to controlling a bending movement of the bending section; and a connecting wire comprising a first end connected to the first input wheel and a second end connected to the second input wheel, wherein the first steering wire, the second steering wire and the third steering wire are each radially spaced from the insertion cord axis and are angularly spaced with respect to each other in a circumferential direction of the insertion cord, and wherein:

the first input wheel comprises a first wheel portion having a first radius and a second wheel portion having a second radius different than the first radius, the second input wheel comprises a third wheel portion having a third radius and a fourth wheel portion having a fourth radius different than the third radius, the first steering wire is connected to the first wheel portion of the first input wheel and extends in a first circumferential direction of the first input wheel, the second steering wire is connected to the third wheel portion of the second input wheel and extends in a first circumferential direction of the second input wheel, the connecting wire is connected to the second wheel portion of the first input wheel and extends in a second circumferential direction of the first input wheel, and the connecting wire is connected to the fourth wheel portion of the second input wheel and extends in a second circumferential direction of the second input wheel.

15. An endoscope comprising:

a handle;

an insertion cord extending from the handle and configured to be inserted into a patient's body cavity, the insertion cord comprising an insertion tube, a bending section and a distal tip unit and having an insertion cord axis;

a steering mechanism configured to swivel the distal tip unit by bending the bending section, the steering mechanism comprising:

a first input wheel and a second input wheel, the first input wheel and the second input wheel being rotatably supported by the handle and being provided for receiving a rotational input by a user; and exactly three steering wires, including a first steering wire, a second steering wire and a third steering wire, the three steering wires extending through the insertion cord and being connected to the first input wheel and/or the second input wheel to controlling a bending movement of the bending section; and a connecting wire comprising a first end connected to the first input wheel and a second end connected to the second input wheel, wherein the first steering wire, the second steering wire and the third steering wire are each radially spaced from the insertion cord axis and are angularly spaced with respect to each other in a circumferential direction of the insertion cord, and the first input wheel comprises a first wheel portion having a first radius and a second wheel portion having a second radius larger than the first radius, the first steering wire being connected to the first wheel portion of the first input wheel and extending in a first circumferential direction, and the connecting wire being connected to the second wheel portion of the first input wheel and extending in a second circumferential direction that is opposite the first circumferential direction, and the second input wheel comprises a third wheel portion having a third radius and a fourth wheel portion having a fourth radius larger than the third radius, the second steering wire being connected to the third wheel portion of the second input wheel and extending in the first circumferential direction, and the connecting wire being connected to the fourth wheel portion of the second input wheel and extending in the second circumferential direction.

16. The endoscope of claim 15, wherein the steering mechanism further includes a first shaft concentric with the third wheel portion about a rotational axis, the first shaft being connected, in a rotationally fixed manner, to the first input wheel, the first wheel portion, and the second wheel portion.

17. The endoscope of claim 16, wherein the steering mechanism further includes a redirecting member positioned in the handle and connected to the third steering wire, the redirecting member translating in the handle responsive to rotation of the first input wheel and/or the second input wheel.

18. A system comprising the endoscope of claim 1 and a monitor connectable to the endoscope.

* * * * *